(12) United States Patent
Lem et al.

(10) Patent No.: US 7,649,107 B2
(45) Date of Patent: Jan. 19, 2010

(54) PROCESS FOR THE PREPARATION OF CYCLOPENTANONE DERIVATIVES

(75) Inventors: Jorge M. Lem, Geneva (CH); Koenraad P. Vanhessche, Feigères (FR); Cyril Mahaim, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 12/067,882

(22) PCT Filed: Nov. 2, 2006

(86) PCT No.: PCT/US2006/042937

§ 371 (c)(1),
(2), (4) Date: Mar. 24, 2008

(87) PCT Pub. No.: WO2007/056129

PCT Pub. Date: May 18, 2007

(65) Prior Publication Data

US 2008/0214859 A1    Sep. 4, 2008

(30) Foreign Application Priority Data

Nov. 4, 2005  (WO) ............... PCT/US2005/039784

(51) Int. Cl.
*C07C 45/61*   (2006.01)
*C07C 49/757*  (2006.01)
*C07C 49/753*  (2006.01)

(52) U.S. Cl. .................................... 560/122

(58) Field of Classification Search ....................... None
See application file for complete search history.

(56) References Cited

FOREIGN PATENT DOCUMENTS

JP            61017531            1/1986

OTHER PUBLICATIONS

Chapuis et al. Helvetica Chimica Acta, 2005, 88(12), 3069-3088.*
Greene "Protective Groups in Organic Synthesis" published in 1981 by John Wiley & Sons, Inc.*
Greene "protecting Groups in Organic Synthesis" Published in 1981 by John Wiley and Sons Inc. p. 124.*
International Search Report & Written Opinion for PCT Application No. PCT/US06/42937.
T. Someya et al., XP009071646, "An Alternative Synthesis Of Methyl Jasmonate", International Congress Of Essential Oils, vol. 7, pp. 1-7, (1977).
T Kitahara et al., XP009071663, "Synthesis Of Jasmine Ketolactone", Agricultural And Biological Chemistry, Agri. Biol. Chem., vol. 48, No. 7, pp. 1731-1734, (1984).

* cited by examiner

*Primary Examiner*—Daniel M Sullivan
*Assistant Examiner*—Yevegeny Valenrod
(74) *Attorney, Agent, or Firm*—Winston & Strawn LLP

(57) ABSTRACT

The present invention relates to the field of organic synthesis and more particularly to a new process for the preparation of an acetal derivative of an alkyl 3-oxo-2-(2-oxoethyl)-1-cyclopentaneacetate. The invention also relates to a method to use said acetal derivative to prepare intermediates useful for the preparation of perfuming ingredients.

18 Claims, No Drawings

PROCESS FOR THE PREPARATION OF CYCLOPENTANONE DERIVATIVES

TECHNICAL FIELD

The present invention relates to the field of organic synthesis and more particularly to a new process for the preparation of an acetal derivative of an alkyl 3-oxo-2-(2-oxoethyl)-1-cyclopentaneacetate. The invention also relates to a method to use the acetal derivative to prepare intermediates useful for the preparation of perfuming ingredients.

PRIOR ART

Alkyl 3-oxo-2-(2-oxoethyl)-1-cyclopentaneacetate, and in particular methyl 3-oxo-2-(2-oxoethyl)-1-cyclopentaneacetate, are known as useful intermediates for the preparation of the perfuming ingredients methyl jasmonate or methyl epi-jasmonate (e.g. see Tanaka et al. in J. Org. Chem., 1975, 462).

However, the synthesis reported in the literature of such compounds suffers from relatively low overall yields due to the fact that they are quite long or involve difficult steps such as ozonolysis (e.g. see Someya T. et al, in "An alternative synthesis of methyl jasmonate", *Internatioial Congress of essential oil*, Vol 7, 1977, pg 1-7) or starting materials which are difficult to prepare.

The present invention aims at providing useful intermediates for the preparation of the above-mentioned aldehyde, as well as the use of some of the intermediates to produce the targeted aldehyde. Another aim is also to provide an alternative process for the preparation of the aldehyde, which offers a relatively short overall process and/or gives similar or higher overall yields.

SUMMARY OF THE INVENTION

The present invention now relates to particular acetals of alkyl 3-oxo-2-(2-oxoethyl)-1-cyclopentaneacetate or malonate, as well as a process to prepare said alkyl 3-oxo-2-(2-oxoethyl)-1-cyclopentaneacetate from said malonate. The invention also relates to a method to use said acetal derivative to prepare intermediates useful for the preparation of perfuming ingredients.

DETAILED DESCRIPTION OF THE PREFERRED EMBODIMENTS

The present invention relates to a process, aimed at the synthesis of a compound of formula (I), in the form of any one of its isomers or a mixture thereof,

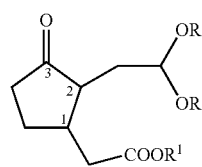
(I)

wherein R represents, taken separately, a $C_1$-$C_5$ alkyl group or, taken together, a $C_2$-$C_6$ alkanediyl group and $R^1$ represents a $C_1$ to $C_4$ alkyl group;

the process comprising a decarboxylation of a compound of formula (II), in the form of any one of its isomers or a mixture thereof,

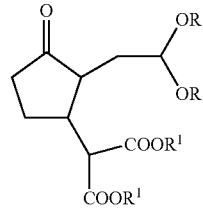
(II)

wherein R and $R^1$ have the meaning indicated in formula (I).

According to one embodiment of the invention, R represents a methyl or ethyl group. According to another embodiment of the invention, $R^1$ represents a methyl or ethyl group. Yet according to a further embodiment of the invention, both R and $R^1$ represent a methyl group.

Although the compounds herein mentioned are represented in a racemic form, which is a valuable form per se, it is understood that in all the above-mentioned embodiments, these compounds can be in the form of any one of its isomers or a mixture thereof. As non-limiting examples of such isomers or mixture thereof, one can cite specifically the cis and trans isomers and in particular the enantiomers having the configuration (1R,2R) or (1R,2S) for compounds of formula (I), (IV), as well as for compounds of formula (III) when $R^2$ is H. Additionally, one can cite specifically the cis or trans isomers and the enantiomers possessing the configuration (1S,2R)- and (1S,2S) for compounds of formula (II).

The compounds of formulae (I) and (II) are also new and inventive compounds, and therefore another object of the invention concerns a compound of formula (III), in the form of any one of its isomers or a mixture thereof,

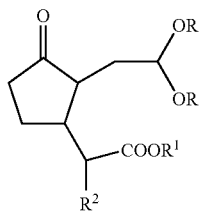
(III)

wherein R and $R^1$ have the meaning indicated above and $R^2$ represents a hydrogen atom or a $COOR^1$ group.

The decarboxylation of compound (II) to provide compound (I) can be promoted by a thermal treatment or by performing a basic saponification and then acidifying the medium.

According to a particular embodiment of the invention a thermal treatment is preferred. In such a case the said thermal treatment can be achieved by heating the reaction medium at a temperature comprised between 120° and 240° C. In another embodiment of the invention the temperature can be comprised between 140° and 190° C.

This thermal treatment may be performed in the presence or absence of a solvent. As non-limiting examples of solvents, one can cite solvents such as having boiling points above 120° C., or even above 140° C., such as DMSO, DMF or in particular NMP and N-ethylpyrolidone.

As mentioned above the compounds of formula (I) can be useful intermediates for the preparation of a 3-oxo-2-(2-oxoethyl)-1-cyclopentaneacetate. Therefore, another object of the present invention concerns the use of a compound of formula (I), as defined above, for the preparation of a compound of formula (IV), as defined below. In particular it concerns a process for the preparation of a compound of formula (IV), in the form of any one of its isomers or a mixture thereof,

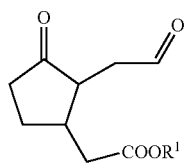

(IV)

wherein $R^1$ has the meaning indicated above;

by treating a compound of formula (I), as defined above, with a Bronsted or Lewis acid.

The acid is advantageously used in the form of a water solution. Non-limiting examples of such acid, are carboxylic acids such as acetic acid, and propionic acid and Lewis acids such as $FeCl_3$ and $LiBF_4$.

Furthermore, this reaction can be carried out at a temperature comprised between 20° and 100° C. In another embodiment of the invention the temperature can be comprised between 30° and 60° C.

The invention's compounds of formula (II) can be prepared according to a process wherein a compound of formula

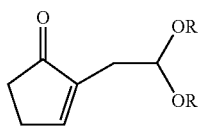

(V)

is reacted with a compound $CH_2(COOR^1)_2$, in the presence of a base, such as a $C_{1-5}$ alcoholate, R and $R^1$ having the meaning provided above. An example of this process is provided further below.

When said compounds of formula (II) are in an optically active form, then they can be obtained by a process identical to the one described above but wherein an optically active phase transfer catalyst (PTC), such as those based on tetraalkyammonium salts, i.e. N-alkylquinidinium or N-alkylcinchonidinium halide salts, as described by Plaquevent et al in *Org. lett.*, 2000, 2, 2959, are used.

The compounds of formula (V) can be obtained according to the method described by Corey et al, in *J. Am. Chem. Soc.*, 1988, 110, 649.

EXAMPLES

The invention will now be described in further detail by way of the following examples, wherein the abbreviations have the usual meaning in the art, the temperatures are indicated in degrees centigrade (° C.); the NMR spectral data were recorded with a 360 MHz machine in $CDCl_3$, the chemical displacement δ are indicated in ppm with respect to the TMS as standard, the coupling constant J are expressed in Hz and all the abbreviations have the usual meaning in the art.

Example 1

Synthesis of dimethyl [2-(2,2-dimethoxyethyl)-3-oxocyclopentyl]malonate

In a 2 liter jacketed reaction flask, a solution of 772 g of 2-(2,2-dimethoxyethyl)cyclopenten-2-one and 864 g dimethylmalonate was cooled to −13° C., then charged with 184 g of a solution NaOMe/MeOH (25 wt. %). Agitation continued for 3.5 hours until the mixture was quenched with 85% $H_3PO_4$. Then the reaction medium was charged with 500 ml of water, and after agitation, the organic phase was recovered. The phase was then washed with water and concentrated to provide the desired crude product. Purification of the crude product by distillation (b.p.=155-156° C. at 1 mbar) provides the title compound with a yield of 92%.

$^1$H-NMR: 4.55 (t, J=6, 1H), 3.766 (s, 3H), 3.761 (s, 3H), 3.70 (d, J=7, 1H), 3.30 (s, 3H), 3.29 (s, 3H), 1.76-2.68 (complex m, 8H)

$^{13}$C-NMR: 218.02, 169.03, 168.52, 102.78, 53.45 (broad), 53.21, 52.56, 52.39, 48.39, 41.18, 36.95, 31.42, 24.12

Synthesis of optically active (1S)-dimethyl [2-(2,2-dimethoxyethyl)-3-oxocyclopentyl]malonate In a 25 ml 1-neck round bottom flask, were charged 2-(2,2-dimethoxyethyl)cyclopenten-2-one (typically 0.5 moles), 10 molar equivalents of dimethyl malonate, 0.1 molar equivalents of N-methylanthtracenylquinidinium chloride and 0.14 molar equivalents of KOH and stirred at 0° C. for 20 hours. The action mixture was poured into a separatory funnel containing 150 ml of ether and washed organic mixture with 0.1N HCl (2×40 ml), followed by water (1×60 ml) and brine (2×60 mL). The organic layer were dried over $Na_2SO_4$ and the solvent stripped off to obtain the crude. Distillation of the crude with a shortpath distillation apparatus provided the desired product with a trans/cis ratio of 95/5. The yield of (1S)-dimethyl [2-(2,2-dimethoxyethyl)-3-oxocyclopentyl] malonate was 78% (based on a 50% conversion of 2-(2,2-dimethoxyethyl)cyclopenten-2-one). The product obtained had an ee=58%.

Example 2

Synthesis of methyl [2-(2,2-dimethoxyethyl)-3-oxocyclopentyl]acetate

In a 3-neck 250 ml round bottom flask equipped with a short path distillation apparatus, a solution of 80.0 g of dimethyl [2-(2,2-dimethoxyethyl)-3-oxocyclopentyl]malonate and 63.0 g NMP was heated to 160° C. The solution was then charged with water until the reaction was complete. Upon completion of the reaction, distillation under vacuum (b.p.=140-145° C. at 1 mbar) of the reaction medium allowed to recover directly the purified title compound with a yield of 81%.

$^1$H-NMR: 4.63-4.61 (m, 1H), 3.70 (s, 1H), 3.32 (s, 3H), 3.31 (s, 3H), 2.75-2.68 (m, 1H), 1.48-2.40 (complex m, 1H)

$^{13}$C-NMR: 218.90, 172.68, 102.68, 53.43, 53.13, 51.64, 50.32, 38.92, 38.47, 37.33, 31.17, 27.42

Synthesis of optically active methyl (1R)-[2-(2,2-dimethoxyethyl)-3-oxocyclopentyl]acetate Same as the racemic version except that (1S)-dimethyl [2-(2,2-dimethoxyethyl)-3-oxocyclopentyl]malonate was used. The yield was 71%, with a trans/cis ratio of 95/5 and an ee=58%.

Example 3

Synthesis of methyl 3-oxo-2-(2-oxoethyl)-1-cyclopentaneacetate

In a 4 liter jacketed reactor, a mixture of 1,236 liter of AcOH and 1,236 liter of water was heated to 45° C. Then to this mixture were added 494 g of methyl [2-(2,2-dimethoxyethyl)-3-oxocyclopentyl]acetate. The resulting reaction medium was stirred at 46-49° C. until completion of the conversion of the acetal to aldehyde. Distillation under vacuum allowed for the direct isolation of the purified title compound with a yield of 89% (overall yield from Example 1: 66%).

$^1$H-NMR: 9.75 (s, 1H), 3.68 (s, 3H), 1.52-2.92 (complex m, 10H)

$^{13}$C-NMR: 217.75, 199.95, 172.54, 51.69, 49.16, 42.32, 38.60, 38.38, 37.00, 27.60.

Synthesis of (1R)-methyl 3-oxo-2-(2-oxoethyl)-1-cyclopentaneacetate

Same as the racemic version except that (1R)-methyl 3-oxo-2-(2-oxoethyl)-1-cyclopentaneacetate was used. The yield was 90%, with a trans/cis ratio of 95/5, and an ee=58%.

What is claimed is:

1. A compound of formula (III),

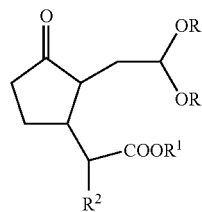

(III)

wherein R represents, taken separately, a $C_1$-$C_5$ alkyl group or, taken together, a $C_2$-$C_6$ alkanediyl group, $R^1$ represents a $C_1$ to $C_4$ alkyl group and $R^2$ represents a hydrogen atom or a COOR$^1$ group.

2. A compound according to claim 1, wherein R and R$^1$ represent a methyl group.

3. A compound according to claim 1, wherein R and R$^1$ represent a methyl group and is in the form of an enantiomer of the configuration (1R,2S) and (1R,2R) if R$^2$ represents a hydrogen atom or (1S,2R) and (1S,2S) if R$^2$ represents a COOR$^1$ group.

4. A process for the preparation of a compound of formula (III) according to claim 1 wherein R$^2$ is hydrogen, wherein the compound is

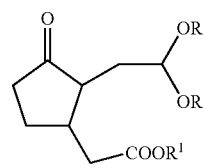

(I)

the process comprising a decarboxylation of a compound of formula (II), in the form of any one of its isomers or a mixture thereof,

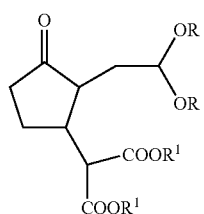

(II)

wherein R and R$^1$ have the meaning indicated in formula (III).

5. A process according to claim 4, wherein R and R$^1$ represent a methyl group.

6. A process according to claim 4, wherein R and R$^1$ represent a methyl group and compounds (II) and (III) are in the form of an enantiomer of the configuration (1R,2S) or (1R,2R) or, respectively, (1S,2R) or (1S,2S).

7. A process according to claim 4, wherein the decarboxylation is achieved by heating the reaction medium at a temperature comprised between 120° and 240° C.

8. A process according to claim 4, wherein the reaction is performed in the presence of NMP as solvent.

9. A process for the preparation of a compound of formula (IV),

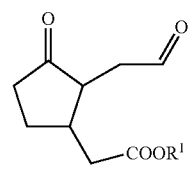

(IV)

wherein R$^1$ represents a $C_1$ to $C_4$ alkyl group;
which comprises treating a compound of formula (I),

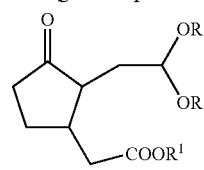

(I)

wherein R represents, taken separately, a $C_1$-$C_5$ alkyl group or, taken together, a $C_2$-$C_6$ alkanediyl group and R$^1$ represents a $C_1$ to $C_4$ alkyl group;
with a Bronsted or Lewis acid 10. A method according to claim 9, wherein R and R$^1$ represent a methyl group and compounds (I) and (IV) are in the form of an enantiomer of the configuration (1R,2S) or (1R,2R). .

11. A compound according to claim 1, wherein $R^2$ is hydrogen.

12. A compound according to claim 11, wherein R is a methyl group.

13. A compound according to claim 11, wherein the R moieties, taken together, form a $C_2$-$C_6$ alkanediyl group.

14. A compound of formula (III),

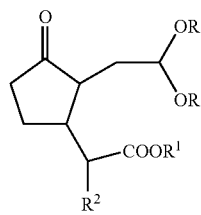

(III)

wherein R represents, taken separately, a $C_1$-$C_5$ alkyl group or, taken together, a $C_2$-$C_6$ alkanediyl group, $R^1$ represents a $C_1$ to $C_4$ alkyl group and $R^2$ represents a $COOR^1$ group.

15. A compound according to claim 14, wherein each $R^1$ is a methyl group.

16. A compound according to claim 15, wherein R is a methyl group.

17. A compound according to claim 15, wherein the R moieties, taken together, form a $C_2$-$C_6$ alkanediyl group.

18. A compound according to claim 1, wherein $R^1$ is a $C_2$ to $C_4$ alkyl group.

* * * * *

UNITED STATES PATENT AND TRADEMARK OFFICE
CERTIFICATE OF CORRECTION

PATENT NO.        : 7,649,107 B2
APPLICATION NO.   : 12/067882
DATED             : January 19, 2010
INVENTOR(S)       : Lem et al.

It is certified that error appears in the above-identified patent and that said Letters Patent is hereby corrected as shown below:

Column 5-6:
Lines 66-67, delete "wherein the compound is".
Lines 1-10, delete the structure of formula (I).
Lines 12-13 (lines 2 and 3 following the deleted structure (I)), delete "in the form of any one of its isomers or a mixture thereof,".

Column 5-6, Claim 4 will then correctly appear as follows:

4.   A process for the preparation of a compound of formula (III) according to claim 1 wherein $R^2$ is hydrogen, the process comprising a decarboxylation of a compound of formula (II),

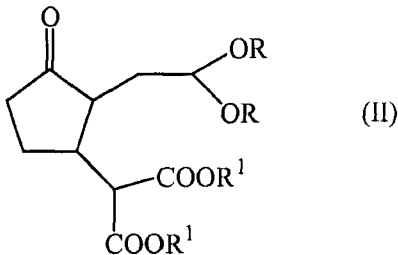

wherein R and $R^1$ have the meaning indicated in formula (III).

Column 6:
Line 67, after "(1R,2R).", delete ".".

Signed and Sealed this

Second Day of March, 2010

David J. Kappos
*Director of the United States Patent and Trademark Office*